United States Patent [19]

Gregory et al.

[11] 4,032,633

[45] June 28, 1977

[54] POLYPEPTIDES

[75] Inventors: Harold Gregory, Macclesfield; Beryl Margaret Preston, Knutsford, both of England

[73] Assignee: Imperial Chemical Industries Limited, London, England

[22] Filed: Aug. 18, 1975

[21] Appl. No.: 605,299

[30] Foreign Application Priority Data

Sept. 11, 1974 United Kingdom ............. 39599/74

[52] U.S. Cl. ......................... 424/177; 260/112.5 R; 195/29
[51] Int. Cl.$^2$ ....................................... A61K 37/00
[58] Field of Search ............. 260/112.5 R; 424/177

[56] References Cited

OTHER PUBLICATIONS

Lawrence et al. *Chem. Abstracts* 74:85914b (1971).

*Primary Examiner*—Delbert R. Phillips
*Attorney, Agent, or Firm*—Cushman, Darby & Cushman

[57] ABSTRACT

A polypeptide having 47 amino-acid residues which is obtained by enzymic degradation of urogastrone. The polypeptide obtained is a potent inhibitor of the secretion of acidic gastric juice and is of value in the treatment of duodenal ulcers.

5 Claims, No Drawings

POLYPEPTIDES

This invention relates to polypeptides which possess the property of inhibiting the secretion of acidic gastric juice.

It has been known for many years that extracts of human urine could cause inhibition of the secretion of acidic gastric juice in warm-blooded animals, and the isolation of two of the active components in pure form is described in German Offenlegungsschrift No. 2,359,564. These two pure components are known as β-urogastrone and γ-urogastrone respectively. The basis of the present invention is the discovery that enzymic degradation of β- or γ-urogastrone can lead to a new polypeptide, and that both the new polypeptide and its reduction product are potent inhibitors of the secretion of acidic juice.

According to the invention there is provided a polypeptide which is a white, water soluble, acidic polypeptide consisting of a single polypeptide chain with three internal disulphide bonds; showing aspartic acid at the N-terminus on dansylation hand having leucine at the C-terminus; having a molecular weight of about 5,500; showing the following physical properties.

paper chromatography in n-butanol: acetic acid: pyridine: water (30:6:24:20) - single spot with mobility of 0.90 relative to phenylalanine; paper electrophoresis in acetic acid/formic acid at pH 2.1 - a 'comet' with front mobility of 1.58 relative to ε-DNP-lysine; acrylamide gel electrophoresis in 0.1 M tris/hydrochloric acid buffer at pH 8.9 - a single spot moving towards the anode with a mobility of 0.81 relative to bromophenol blue;

giving an amino-acid ratio on analysis of a hydrolysate of:

aspartic acid 7, serine 3, glutamic acid 4, proline 1, glycine 4, alanine 2, valine 3, cysteine 6, methionine 1, isoleucine 2, leucine 4, tyrosine 5, histidine 2, lysine 1, and arginine 2;

and having a biological potency, as defined later, in the range 0.2 to 1 μg./kg.;

or the reduction product in which the cystine residues are reduced to cysteine residues.

According to a further feature of the invention there is provided a process for the manufacture of the polypeptide of the invention which comprises exposing β-urogastrone or γ-urogastrone in an aqueous medium to the action of a lysine specific amino-endopeptidase followed by separation of the required polypeptide from the reaction mixture, whereafter when the reduction product is desired, the polypeptide so obtained is reduced with a reducing agent conventionally used in peptide chemistry for the reduction of disulphide bonds, for example a thiol, for example mercaptoethanol or dithiothreitol.

An example of a suitable lysine specific aminoendopeptidase is the enzyme AM protease which may be obtained from the mature fruiting bodies of the fungus *Armilaria mellea* as fully described and claimed in U.K. Pat. specification No. 1,263,956.

The exposure of the β- or γ-urogastrone to the lysine specific amino-endopeptidase may be carried out with the enzyme simply dissolved in the aqueous medium, or it may be carried out with the enzyme bound to a support which may or may not be soluble in the aqueous medium.

The rate and extent of the reaction between the urogastrone, i.e. β- or γ-urogastrone, used as starting material and the enzyme is dependent upon the enzyme/substrate ratio, the pH and temperature of the incubation medium, the concentration of the urogastrone and the time of incubation. In general, of course, the time taken to cleave the urogastrone is shortened by an increase in either the concentration of the urogastrone or the enzyme/substrate ratio. Similarly, variation in the pH or temperature of the incubation medium affects the time of cleavage. The progress of the reaction may be followed by examining samples of the reaction medium using paper electrophoresis at pH 6.5 or by subjecting the samples to the "dansylation" technique using 1-dimethylaminonaphthalene-5-sulphonyl chloride (Hartley, Biochem. J. 1970, 119, 805) and estimating the amount of $N^{\alpha}$, $N^{\epsilon}$-dansyl-L-lysine formed. Thus the effect of any variation in the reaction conditions can be determined.

In general, the reaction will proceed at a wide variety of enzyme/substrate ratios, but a minimum ratio of 1 part of enzyme to 1,000 parts of substrate is desirable. The reaction will proceed at a pH of the incubation medium from 3 to 10, and at a temperature from 10° C. to 50° C. Preferred conditions to obtain the desired cleavage of the urogastrone in a relatively short time, for example 12-24 hours, are a concentration of urogastrone from 1 mg./ml. upwards, a pH from 6 to 9, a temperature from 20° C. to 40° C., and an enzyme/substrate ratio of from 1 part of enzyme to 8 parts of substrate to 1 part of enzyme to 100 parts of substrate. It is also convenient to include metal ions in the incubation medium, for example calcium or magnesium ions in the form of their chlorides at a concentration of $10^{-2}$ to $10^{-4}$ molar.

The effect of the lysine specific amino-endopeptidase on the β- or γ-urogastrone is, of course, to cleave the β- or γ-urogastrone on the amino side of a lysine residue. While the starting urogastrone contains two lysine residues, it has been found that the cleavage takes place predominantly at one of the lysine residues. From β-urogastrone, a hexapeptide containing one glutamic acid, one leucine, one lysine, two tryptophan and one arginine residue, with lysine at the N-terminus, is liberated, and from γ-urogastrone, a pentapeptide containing one glutamic acid, one leucine, one lysine and two tryptophan residues, with lysine at the N-terminus, is liberated. However, under some of the more severe reaction conditions, some cleavage at the other lysine residue can occur and lead to a second polypeptide in the product.

The polypeptides remaining after cleavage of the hexa- or pentapeptide respectively from β- or γ-urogastrone are identical and constitute the polypeptide of the invention. This polypeptide may be separated from the reaction mixture by any conventional technique for the separation of polypeptides, but the use of gel chromatography is particularly convenient. Thus the aqueous medium remaining after cleavage of the hexa- or pentapeptide from the β- or γ-urogastrone respectively may be filtered through a column of cross-linked dextran gel or a polyacrylamide gel and the column eluted with a buffer composed of components which are volatile on freeze drying under high vacuum, for example, an aqueous ammonium acetate solution having a pH of 7.2, to give the desired product which is isolated by freeze drying the eluate.

When the reduction product is required, the polypeptide of the invention is conveniently reduced in an aqueous buffer at a pH from 7 to 10, and with the exclusion of oxygen and light. The product may again be isolated by using gel chromatography.

As indicated above, the polypeptide of the invention and its reduction product are potent inhibitors of the secretion of acidic gastric juice in warm blooded animals. This property is demonstrated by their action in inhibiting the secretion of acidic gastric juice in dogs provided with a Heidenhain pouch and whose gastric secretion is stimulated with histamine. This test is used to determine the biological potency of the products, which is defined as the amount of the product expressed in $\mu$g./kg. which, on administration by intravenous injection to a dog provided with a Heidenhain pouch and whose secretion of gastric acid is stimulated to 60–89% of the maximum level of secretion by an infusion of histamine, causes a 50–70% inhibition of that acid secretion. Some variation in the biological potency of a particular sample is found if it is measured in different dogs and on different occasions, and so the result is best expressed as a dose range. The physiological effect of inhibiting the secretion of acidic gastric juice is of a value in the treatment of duodenal ulcers, and under the test conditions, no serious toxic effects were observed. The polypeptides also show ulcer healing properties in a standard test.

When used to produce an inhibition of the secretion of acidic gastric juice in warm blooded animals, a wide range of doses may be used, for example from 0.05 to 10 $\mu$g./kg., depending upon the circumstances and extend of inhibition required. The dose may be administered by injection, especially intravenous or subcutaneous injection, or by intravenous infusion. The effect of a single intravenous injection lasts for about 1½ hours and the effect of an infusion lasts for about 1½ hours after completion of the infusion, so maintenance of a low level of acidity requires either that the dose be repeated or that a depot formulation be injected from which the active ingredient is released slowly over a more prolonged period of time. When used in man, typical single dose is from 5 to 500 $\mu$g./man administered by injection or infusion.

The polypeptide or reduction product of the invention may be administered in the form of a pharmaceutical composition, so according to a further feature of the invention there is provided a pharmaceutical composition comprising the polypeptide or reduction product as defined above and a pharmaceutically acceptable diluent or carrier.

Preferred compositions are those suitable for parenteral administration, for example sterile, injectable solutions or suspensions, and sterile injectable depot or slow-release formulations. An injectable solution or suspension may contain from 0.5 to 500 $\mu$g./ml., the more dilute solutions being administered by infusion, but an injectable depot or slow-release formulation may contain up to 2 mg. of active ingredient per dose. Particularly convenient sterile, injectable solutions are made up in isotonic saline or isotonic dextrose, buffered if necessary to a pH from 5 to 9, and may contain from 1 to 100 $\mu$g./ml.

The sterile, injectable compositions referred to above may be prepared and stored as such or they may be prepared immediately before use by adding a sterile medium, for example water, to a known weight, for example 10 to 200 $\mu$g., of sterile ingredient enclosed in a vehicle, for example vial or ampoule, which maintains its sterility. The known weight of sterile ingredient may also contain sufficient sterile dextrose or sodium chloride to give an isotonic solution after dilution with the sterile medium.

The invention is illustrated but not limited by the following Examples in which the specific chromatography materials referred to by manufacturer's trade mark or code are available as follows:

a porous ployacrylamide gel, Biogel P6 from Bio-Rad Laboratories, Richmond, Calif., porous cross-linked dextran gel, Sephadex G-25 from Pharmacia Fine Chemicals AB, Uppsala, Sweden.

In the case of each process involving the use of a chromatography column, the eluate was collected in fractions consisting of a defined number of drops using an Ultrorac LKB 7,000 fraction collector (LKB Instruments Ltd., Croydon, Surrey, U.K.) and these fractions assayed for peptide material by measuring the U.V. absorption at 280 m$\mu$. The material was then collected in fractions and the material assayed for biological activity as follows:

Dogs were prepared with separated denervated fundic pouches, and a subcutaneous infusion of histamine was used to stimulate gastric secretion to approximately 60–80% of the maximal rate [usually an infusion of a solution of 600 $\mu$g. of histamine (expressed as base) in 0.48 ml. per hours was adequate]. A known amount of test material was dissolved in isotonic saline and, when the dog was secreting gastric juice at a steady rate, a single intravenous injection of this material was administered. The inhibition of gastric secretion was noted for the particular dose tested.

The specific activity may be determined from the results obtained for several different doses.

Amino-acid analyses were carried out using a Locarte Amino-acid Analyser (Locarte Ltd., 24 Emperors Gate, London S.W.7).

All column chromatography was carried out at 4° C., and all the buffer solutions were saturated with toluene.

EXAMPLE 1

A solution of $\beta$-urogastrone (1.0 mg.) in a mixture of 0.1 M ammonium bicarbonate buffer of pH 8.2 (200 $\mu$l.) and 0.01 magnesium chloride solution (50 $\mu$l.) was incubated with AM protease (60 $\mu$g.) in water (200 $\mu$l.) for 16 hours at 37° C. The resulting solution was applied to a column (35 × 1 cm.) of porous cross-linked dextran gel (Sephadex G-25) and the column developed with 0.05 M ammonium acetate at a flow rate of 8 ml./hr. Fractions of 1 ml. were collected and peptidic material was detected in fractions 12–20 and 38–52.

The material in fractions 38–52 was biologically inactive and samples were hydrolysed with acid, base or leucineaminopeptidase. Analysis of the resulting solutions showed that the original peptide contained amino-acids in the following ratios: Glu 1, Leu 1, Lys 1, Trp 2, Arg 1. Dansylation showed the presence of lysine at the N-terminus.

The material from fractions 12–20 was biologically active, and these fractions were combined and lyophilised to give a white, water soluble, acidic polypeptide having the following properties:

1. biological activity on a single determination: 30% inhibition at a dose equivalent to 0.7 $\mu$g./kg. of starting material.

2. amino acid ratios on analysis of a hydrolysate: Asp 7, Ser 3, Glu 4, Pro 1, Gly 4, Ala 2, Val 3, Cys 6, Met 1, Ile 2, Leu 4, Tyr 5, His 2, Lys 1, Arg 2.

3. single spot with mobility of 0.90 relative to phenylalanine on paper chromatography in n-butanol: acetic acid:pyridine:water (30:6:24:20).

4. a 'comet' with front mobility of 1.58 relative to ε-DNP-lysine on paper electrophoresis in acetic acid/formic acid at pH 2.1 (20 ml. formic acid, 80 ml. acetic acid made up to 1 litre with water).

5. single spot with mobility of 0.81 relative to bromophenol blue on acrylamide gel electrophoresis in 0.1 M tris-hydrochloric acid buffer at pH 8.9.

Dansylation of the product showed the presence of aspartic acid at the N-terminus, and digestion with carboxypeptidase A showed the presence of leucine at the C-terminus.

Dansylation of the product did however show the presence of a small amount of a peptide having lysine at the N-terminus indicating the presence of a small amount of peptide formed by cleavage at the second lysine residue of the starting material.

EXAMPLE 2

A solution of γ-urogastrone (1.8 mg.) in a mixture of 0.1 M ammonium bicarbonate buffer of pH 8.2 (200 μl.) and 0.1 M calcium chloride solution (20 μl.) was incubated with AM protease (100 μg.) in 0.1 M ammonium bicarbonate solution (100 μl.) at 37° C. for 3 hours. A second portion of AM protease (100 μg.) was added and the incubation continued for a further 16 hours. The resulting solution was applied to a column (35 × 1.1 cm.) of porous cross-linked dextran gel (Sephadex G-25) and the column developed with 0.05 M ammonium acetate at a flow rate of 17 ml./hr. Fractions of 30 drops were collected, and peptidic material was detected in fractions 15–24 and 49–65.

The material in fractions 49–65 was biologically inactive and analysis of hydrolysates showed that the material contained amino-acids in the following ratios: Glu 1, Leu 1, Lys 1, Trp 2. Dansylation showed the presence of lysine at the N-terminus.

The material from fractions 15–24 was biologically active, and these fractions were combined and lyophilised to give a white, water soluble, acidic polypeptide, the same as that obtained in Example 1.

EXAMPLE 3

A solution of β-urogastrone (1.75 mg.) in 0.025 M ammonium bicarbonate (1.0 ml.) was incubated with AM protease (30 μg.) in water (100 μl.) at 37° C. for 3 hours. A second portion of AM protease (20 μg.) was then added and the incubation continued for a further 16 hours. The resulting solution was applied to a column (100 × 0.9 cm.) of porous polyacrylamide gel (Biogel P6: 200-400 mesh) equilibrated with 0.05 M ammonium acetate. The column was developed with this solution at a flow rate of 5 ml./hr. Fractions of 1 ml. were taken and the biologically active peptidic material was detected in fractions 24–30. These were combined and lyophilised to give a white, water soluble, acidic polypeptide with the same properties as the product of Example 1; showing a biological activity on a single determination of 67% inhibition at a dose equivalent to 0.6 μg./kg. of starting material.

EXAMPLE 4

The whole of the polypeptide obtained in Example 3 was dissolved in water and urea (100 mg.), ethylenediaminetetra-acetic acid (1 mg.), and 1.5 M tris-hydrochloric acid buffer of pH 8.6 (100 μl.) were added. The solution was diluted to 250 μl. with water, flushed with nitrogen containing no oxygen and then dithiothreitol (10 mg.) added. The resulting solution was kept in the dark for 20 hours and then applied to a column (100 × 0.9 cm.) of porous polyacrylamide gel (Biogel P6; 200–400 mesh) equilibrated with 0.05 M ammonium acetate containing 0.0002 M dithiothreitol. The column was developed with this solution at a flow rate of 5 ml./hr. Fractions of 1 ml. were collected and the peptidic material was detected in fractions 24–33. The material from these fractions was biologically active and these fractions were combined and lyophilised to give a polypeptide in which the cystine residues had been reduced to cysteine residues and which had the following properties:

1. biological activity on a single determination: 59% inhibition at a dose equivalent to 0.6 μg./kg. of starting material.

2. amino-acid ratios on analysis of a hydrolysate: Asp 7, Ser 3, Glu 4, Pro 1, Gly 4, Ala 2, Val 3, Cys 6, Met 1, Ile 2, Leu 4, Tyr 5, His 2, Lys 1, Arg 2.

EXAMPLE 5

The polypeptide described in Example 1 or a reduction product thereof in which the original cystine residues are reduced to cysteine, is dissolved in pyrogen free 5% w/v dextrose solution to give a final concentration of 40 μg./ml. This solution is dispensed into vials in aliquots of 2.5 ml. each through a sterilising membrane filtration system, for example a 0.22 mμ 'Millipore' ('Millipore' is a trade mark) filter. The contents of each vial are then lyophilised and the vials capped and sealed under sterile conditions. The vials containing a sterile mixture of polypeptide and dextrose are stored at 4° C.

EXAMPLE 6

To a vial prepared as described in Example 5 is added 2.5 ml. of sterile water immediately before use to give a sterile injectable solution of 40 μg./ml. of polypeptide in 5% w/v dextrose solution.

EXAMPLE 7

The polypeptide described in Example 1 or a reduction product thereof in which the original cystine residues are reduced to cysteine, (10 mg.) is dissolved in pyrogen-free water (50 ml), and the solution is filtered through a sterilising membrane filtration system, for example a 0.22 mμ. 'Millipore' filter ('Millipore' is a trade mark), into ampoules so that each ampoule receives 0.5 ml. The contents of each ampoule are then lyophilised, and the ampoules sealed under sterile conditions. The ampoules, each containing 100 μg. of sterile polypeptide, are kept at −20° C.

EXAMPLE 8

The contents of an ampoule, prepared as in Example 7, are dissolved in sterile, pyrogen-free 5% w/v dextrose solution to give a solution containing from 1 to 5 μg./ml. of polypeptide in 5% w/v dextrose solution. This solution is suitable for administration by infusion.

If a solution suitable for injection is required, the contents of an ampoule are dissolved in sterile, pyrogenfree 5% w/v dextrose solution to give a solution containing 5-50 μg./ml. of polypeptide Alternatively, the 5% w/v dextrose solution may be replaced by isotonic saline.

The polypeptide of the invention has been studied by the methods used to determine the structure of polypeptides, and the following structure has been found:

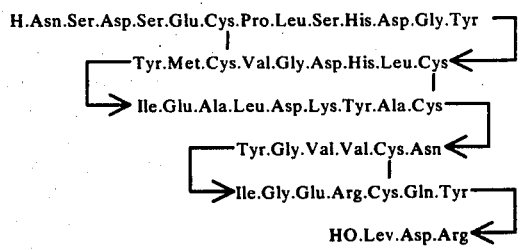

What we claim is:
1. The polypeptide of the formula:

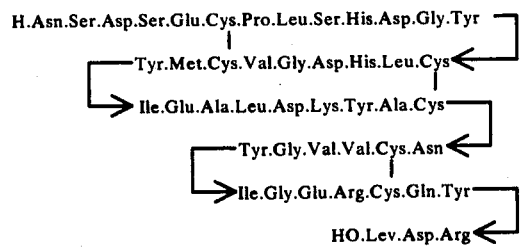

or its reduction product in which the cystine residues are reduced to cysteine residues.

2. A pharmaceutical composition for parenteral administration comprising a polypeptide or reduction product as defined in claim 1 and a pharmaceutically acceptable diluent or carrier.

3. A composition as claimed in claim 2 which is a sterile, injectable solution or suspension containing from 0.5 to 500 μg./ml. of polypeptide or reduction product.

4. A pharmaceutical composition comprising from 10 to 200 μg. of sterile polypeptide or reduction product as defined in claim 1 enclosed in a vial or ampoule which maintains its sterility.

5. A method of inhibiting the secretion of acidic gastric juice in warm blooded animals which comprises administering to said animal an effective amount of a polypeptide or reduction product as defined in claim 1.

* * * * *